United States Patent [19]

Kobayashi

[11] Patent Number: 5,170,796

[45] Date of Patent: Dec. 15, 1992

[54] PULSE WAVE DETECTING APPARATUS

[75] Inventor: Ikuo Kobayashi, Koganei, Japan

[73] Assignee: Colin Electronics Co., Ltd., Aichi, Japan

[21] Appl. No.: 657,870

[22] Filed: Feb. 20, 1991

[30] Foreign Application Priority Data

Mar. 1, 1990 [JP] Japan .................................. 2-50122

[51] Int. Cl.⁵ .............................................. A61B 5/02
[52] U.S. Cl. .................................................. 128/687
[58] Field of Search .................................. 128/687–690

[56] References Cited

U.S. PATENT DOCUMENTS

| | | | |
|---|---|---|---|
| 3,985,121 | 10/1976 | Hellenbrand | 128/689 |
| 4,836,213 | 6/1989 | Wenzel et al. | 128/672 |
| 4,934,372 | 6/1990 | Corenman et al. | 128/633 |
| 4,938,228 | 7/1990 | Righter et al. | 128/690 |
| 5,000,188 | 3/1991 | Kojima | 128/687 |

FOREIGN PATENT DOCUMENTS 64-12505 1/1989 Japan .
1-209045 8/1989 Japan .

Primary Examiner—Lee S. Cohen
Assistant Examiner—Kevin Pontius
Attorney, Agent, or Firm—Oliff & Berridge

[57] ABSTRACT

A pulse wave detecting apparatus, including a pulse wave sensor having a press surface on which a plurality of pressure sensing elements are provided in an array, a main device receiving an electric signal from each of the pressure sensing elements, a determining device determining a correlation between a distribution of magnitudes of the electric signals as taken along the array of pressure sensing elements, and each of a plurality of predetermined reference distributions which is indicative of a corresponding one of a plurality of different relative positions of the array of pressure sensing elements with respect to the blood vessel, a selecting device selecting one of the reference distributions which provides the greatest correlation of all the correlations determined by the determined device, and a transmitting device transmitting to the main device the electric signals generated from the pressure sensing elements in a portion of the array of pressure sensing elements which portion corresponds to the relative position indicated by the reference distribution selected by the selecting device.

9 Claims, 3 Drawing Sheets

PULSE WAVE DETECTING APPARATUS

BACKGROUND OF THE INVENTION

1. Field Of The Invention

The present invention generally relates to a pulse wave detecting apparatus and particularly to such an apparatus which has a pulse wave sensor including a plurality of pressure sensing elements.

2. Related Art Statement

There is known a pulse wave detecting apparatus of a type which includes (a) a pulse wave sensor having a press surface on which a plurality of pressure sensing elements are provided in an array, the pulse wave sensor being adapted to be pressed at the press surface against a body surface of a subject such that the array of pressure sensing elements crosses over a blood vessel underlying the body surface, each of the pressure sensing elements generating an electric signal representative of a pulse wave transmitted thereto from the blood vessel via the body surface; and (b) a main device receiving the electric signal from the each of the pressure sensing elements In this apparatus, the main device comprises a microcomputer including a central processing unit (CPU). The CPU processes the electric signals, i.e., pulse wave signals supplied from the pressure sensing elements. Based on the shape of a curve representative of a distribution of magnitudes or voltages of the pulse wave signals as taken along the direction of the array of pressure sensing elements, the CPU determines an optimum pressing force to press the pulse wave sensor against the body surface or blood vessel, at which force the blood vessel is deformed to be partially flat, and determines an optimum pressure sensing element, i.e., middle one of the pressure sensing elements positioned directly above the width or lumen of the blood vessel being partially flat, which element generates an optimum or most accurate pulse wave signal. An example of this apparatus is disclosed in the Publication No. 64-12505 of unexamined Japanese Utility Model Application filed by the Assignee of the present U.S. patent application.

In the above indicated apparatus, the array of pressure sensing elements is required to have a sufficiently larger length (i.e., distance between the two elements at the opposite ends of the array) than the width of blood vessel, because it would otherwise be so difficult to locate the pulse wave sensor or array of pressure sensing elements in position with respect to the blood vessel. In addition, the array of pressure sensing elements is required to have the smallest possible space between each pair of adjacent elements and thereby improve the resolution of the pulse wave sensor, for the purpose of accurately determining the optimum pressing force to be applied to the pulse wave sensor and/or determining the optimum pressure sensing element from which the optimum pulse wave signal is produced, and additionally for the purpose of eliminating the cases in which the optimum pressure sensing element determined is not a middle one of the pressure sensing elements positioned directly above the blood vessel.

However, the longer the array of pressure sensing elements becomes and/or the smaller the space between the pairs of adjacent pressure sensing elements becomes, the greater number of pressure sensing elements are needed, and the greater number of pulse wave signals are transmitted to the main device. Consequently, a transmission system which couples the pressure sensing elements to the main device to transmit the pulse wave signals therebetween, suffers from increased amount of burden. In addition, the main device suffers from dealing with an increased number of pulse wave signals.

SUMMARY OF THE INVENTION

It is therefore an object of the present invention to provide a pulse wave detecting apparatus which employs an increased number of pressure sensing elements, without increasing burden to a transmission system of the apparatus that couples the pressure sensing elements to a main device of the apparatus to transmit pulse wave signals therebetween, and at the same time without increasing the number of pulse wave signals to be dealt with by the main device.

The above object has been achieved by the present invention, which provides a pulse wave detecting apparatus, comprising (a) a pulse wave sensor having a press surface on which a plurality of pressure sensing elements are provided in an array, the pulse wave sensor being adapted to be pressed at the press surface against a body surface of a subject such that the array of pressure sensing elements crosses over a blood vessel underlying the body surface, each of the pressure sensing elements generating an electric signal representative of a pulse wave transmitted thereto from the blood vessel via the body surface, (b) a main device receiving the electric signal from the each of the pressure sensing elements, (c) determining means for determining a correlation between a distribution of magnitudes of the electric signals as taken along the array of the pressure sensing elements, and each of a plurality of predetermined reference distributions which is indicative of a corresponding one of a plurality of different relative positions of the array of pressure sensing elements with respect to the blood vessel, (d) selecting means for selecting one of the reference distributions which provides the greatest correlation of all the correlations determined by the determining means, and (e) transmitting means for transmitting to the main device the electric signals generated from the pressure sensing elements in a portion of the array of pressure sensing elements which portion corresponds to the relative position indicated by the reference distribution selected by the selecting means.

In the pulse wave detecting apparatus constructed as described above, the determining means determines a correlation between a distribution of magnitudes of the electric signals as taken along the direction of the array of pressure sensing elements, and each of a plurality of predetermined reference distributions which is indicative of a corresponding one of a plurality of different relative positions of the array of pressure sensing elements with respect to the blood vessel, the selecting means selects one of the reference distributions which provides the greatest correlation of all the correlations determined by the determining means, and the transmitting means transmits, to the main device, only the electric signals generated from the pressure sensing elements in a portion of the array of pressure sensing elements which portion corresponds to the relative position indicated by the reference distribution selected by the selecting means.

Even if a large number of pressure sensing elements are used for increasing the length of the array of pressure sensing elements and simultaneously reducing the space between the pairs of adjacent pressure sensing elements, a signal transmission system which transmits to the main device the electric signals generated from the pressure sensing elements is free from increased amount of burden, since the transmission system is required to transmit only a small group of electric signals out of all the electric signals generated from the pressure sensing elements, which group of electric signals are necessary and sufficient for determining an optimum pressing force to press the pulse wave sensor against the body surface and an optimum pressure sensing element which generates an optimum pulse wave signal accurately representing the pulse wave produced from the blood vessel. In addition, the main device is advantageously prevented from dealing with an increased number of pulse wave signals. Each of the pressure sensing elements may comprise a pressure sensing diode. The array of pressure sensing elements extends over a length greater than a lumen of the blood vessel, and each of the pressure sensing elements is smaller than the lumen of the blood vessel.

According to a feature of the present invention, the determining means comprises a plurality of sum-of-products calculation circuits each of which includes an operational amplifier and the same number of weighted resistors as the number of the pressure sensing elements, the weighted resistors of the each calculation circuit having respective weighed resistance values which are representative of a corresponding one of the reference distributions, the reference distributions respectively corresponding to different small groups of pressure sensing elements in different portions of the array of pressure sensing elements.

According to another feature of the present invention, the determining means determines the correlation, $\gamma$, according to the following expression (1):

$$\gamma = \sum_{i=1}^{n} w_i \cdot t_i \tag{1}$$

wherein $w_i$; the weighted resistance values of the weighted resistors of the each calculation circuit, $t_i$; voltages of the electric signals applied to the weighted resistors, and n; number of the pressure sensing elements (equal to the number of the weighted resistors), and generates a signal indicative of the determined correlation value, to the selecting means.

According to yet another feature of the present invention, the selecting means selects one of the reference distributions which provides the greatest correlation value, $\gamma_{max}$, of all the determined correlation values, and generates a signal indicative of the selected reference distribution, to the transmitting means.

According to a further feature of the present invention, the transmitting means comprises the same number of gates as the number of the calculation circuits, and is responsive to the signal from the selecting means to open one of the gates which corresponds to the selected reference distribution and transmit to the main device only the electric signals generated from the group of pressure sensing elements corresponding to the selected reference distribution.

According to another feature of the present invention, the main device comprises a microcomputer and a display, said microcomputer including a central processing unit which processes the electric signals from the group of pressure sensing elements and thereby determines an optimum pressing force to press the pulse wave sensor against the body surface at which force the blood vessel is deformed to be partially flat, and an optimum pressure sensing element out of the pressure sensing elements which produces an electric signal accurately representing the pulse wave, the microcomputer commanding the display to indicate a waveform of the electric signal supplied from the optimum pressure sensing element.

In a preferred embodiment of the present invention, the apparatus further comprises coupling means for coupling the transmitting means to the main device to transmit the electric signals therebetween. The coupling means may comprise a multiplexer.

BRIEF DESCRIPTION OF THE DRAWINGS

The above and optional objects, features and advantages of the present invention will be better understood by reading the following detailed description of the presently preferred embodiments of the invention when considered in conjunction with the accompanying drawings, in which.

DETAILED DESCRIPTION OF THE PREFERRED EMBODIMENTS

Figure 1:
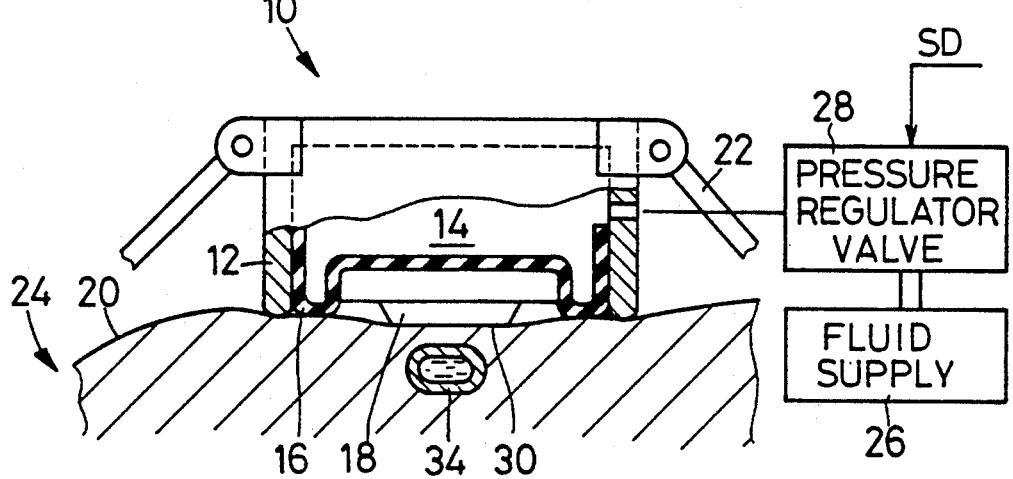
FIG. 1 is an illustrative view, partly in cross section, of a pulse wave detector probe of a pulse wave detecting apparatus of the present invention, the probe being set on a body surface of a subject.
Figure 2:
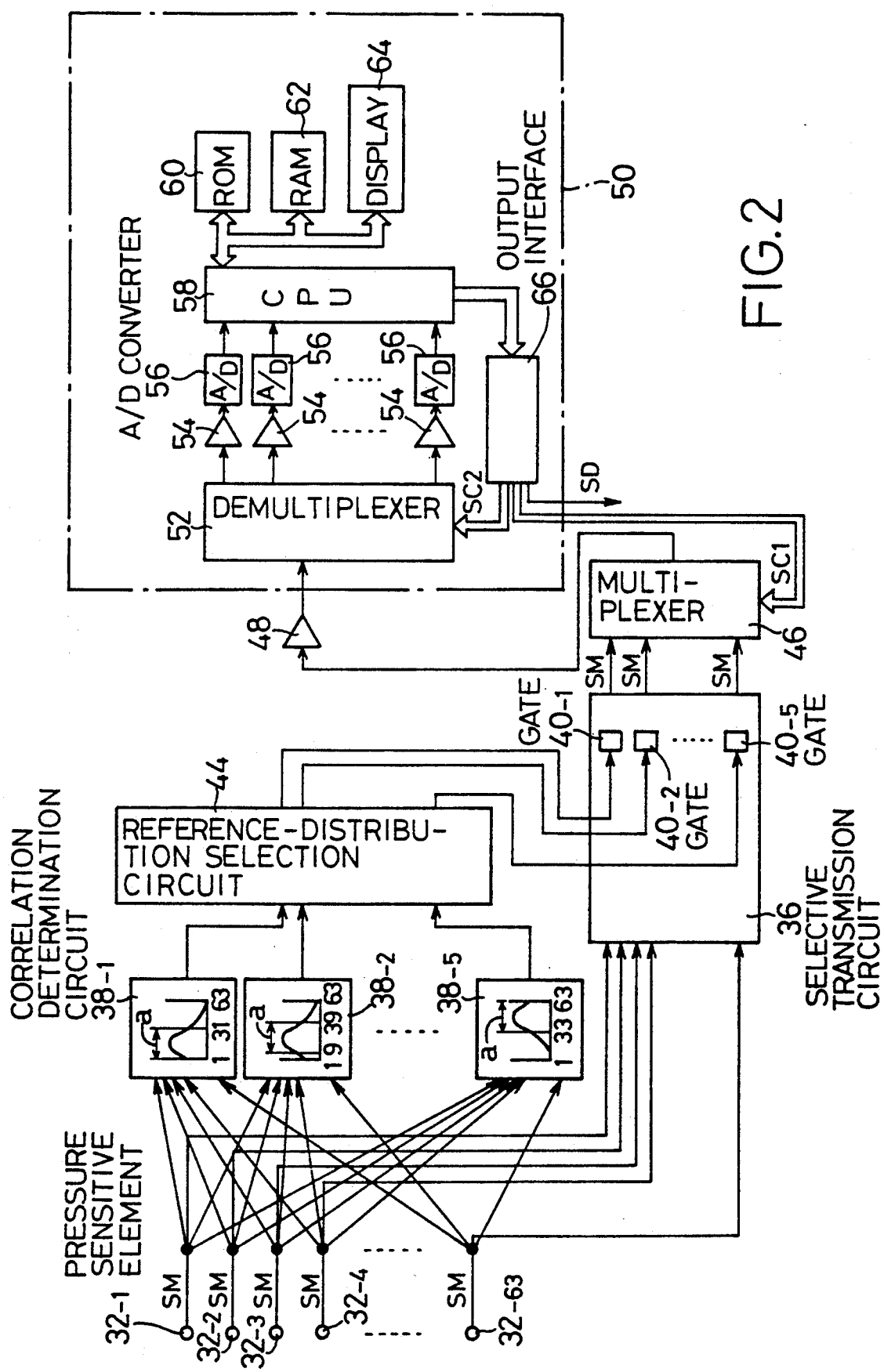
FIG. 2 is a diagrammatic view of the construction of the invention apparatus.
Figure 3:
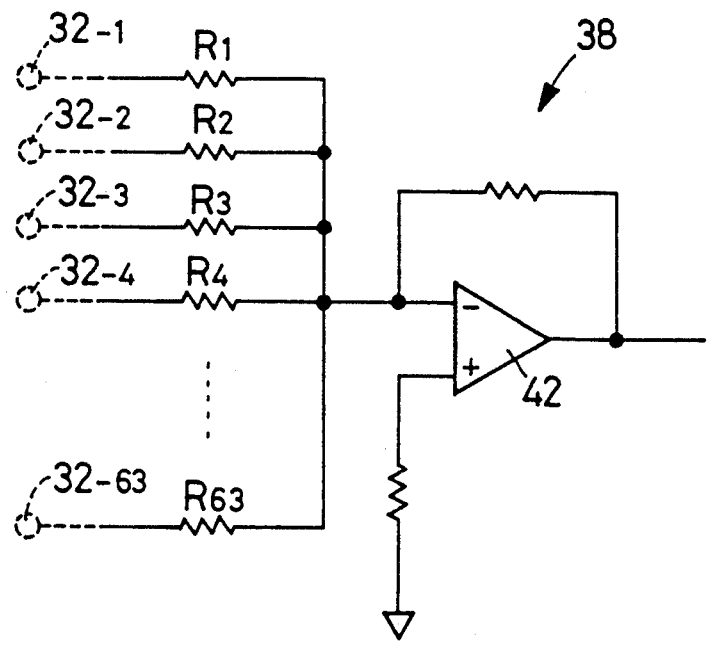
FIG. 3 is a view of a correlation determination circuit employed in the invention apparatus of FIG. 2.

Referring to FIGS. 1, 2 and 3, there is shown a pulse wave detecting apparatus embodying the present invention.

In FIG. 1, reference numeral 10 designates a pulse wave detector probe. The probe 10 includes a cylindrical housing 12, an elastic diaphragm 16, and a pulse wave sensor 18. The cylindrical housing 12 is closed at one of axially opposite ends thereof and is open at the other axial end. The elastic diaphragm 16 is secured at an outer peripheral portion thereof to an inner circumferential surface of the housing 12, so that the diaphragm 16 cooperates with the housing 12 to define a pressure chamber 14 inside the housing 12. The pulse wave sensor 18 is fixed to one of opposite surfaces of the diaphragm 16 which surface is remote from the pressure chamber 14. The sensor 18 is displaceable out of the open end of the housing 12 when the diaphragm 16 is expanded downward as viewed in FIG. 1. The probe 10 is detachably set around a wrist 24 of a subject with the help of a band 22, such that the open end of the housing 12 contacts a surface 20 of the wrist 24. The pressure chamber 14 is supplied with a pressurized fluid such as pressurized air from a fluid supply 26 via a pressure regulator valve 28. Thus, the pulse wave sensor 18 is pressed against the body surface 20 with a pressing force corresponding to a fluid pressure in the chamber 14.

An array of pressure sensing elements 32 (FIG. 2) are provided on a press surface 30 of the pulse wave sensor 18, such that the array of elements 32 extend in a direction. The pressure sensing elements 32 may be arranged in a row along a straight line as disclosed in the previously indicated Publication No. 64-12505 of unexamined Japanese Utility Model Application. Alternatively, the pressure sensing elements 32 may be arranged in two rows in an alternate fashion as disclosed in the Publication No. 1-209045 of unexamined Japanese Patent Application filed by the Assignee of the present U.S. patent application. In the present embodiment, sixty three elements $32_1$ to $32_{63}$ are used, though only five elements 32 are shown in FIG. 2. Pressure sensing diodes may be used as the pressure sensing elements 32. The pulse wave sensor 18 is pressed against the body surface 20 such that the array of pressure sensing elements 32 crosses over the radial artery 34 substantially perpendicular to the direction of extension of the artery 34. Each of the pressure sensing elements 32 detects an oscillatory pressure wave, i.e., pulse wave produced from the radial artery 34 and transmitted thereto via the body surface 20, and generates an electric signal representative of the detected pulse wave. The array of pressure sensing elements 32 extends over a length sufficiently larger than the width or lumen of the radial artery 34. In addition, the dimensions of each of the elements 32 and the space between each pair of adjacent elements 32 are so small as to allow a number of elements 32 to be positioned directly above the artery 34.

As shown in FIG. 2, the electric signal, i.e., pulse wave signal SM generated by each of the pressure sensing elements 32, is supplied to a selective transmission circuit 36 and, at the same time, to each of a plurality of correlation determination circuits 38. In the present embodiment, five correlation determination circuits $38_1$ to $38_5$ are used, though only three circuits 38 are shown in FIG. 2. The selective transmission circuit 36 has the same number of gates 40 as the number of correlation determination circuits 38. In the present embodiment, five gates $40_1$ to $40_5$ are used, though only three gates 40 are shown in FIG. 2. The first gate $40_1$ receives thirty-one pulse wave signals SM from the first to thirty-first pressure sensing elements $32_1$ to $32_{31}$. Similarly, the second gate $40_2$ receives thirty-one signals SM from the ninth to thirty-ninth elements $32_9$ to $32_{39}$; the third gate $40_3$ receives thirty-one signals SM from the seventeenth to forty-seventh elements $32_{17}$ to $32_{47}$; the fourth gate $40_4$ receives thirty-one signals SM from the twenty-fifth to fifty-fifth elements $32_{25}$ to $32_{55}$; and the fifth gate $40_5$ receives thirty-one signals SM from the thirty-third to sixty-third elements $32_{33}$ to $32_{63}$.

Each of the five correlation determination circuits 38 determines a correlation between a distribution of magnitudes or voltage values of all (i.e., sixty-three) pulse wave signals SM as taken along the direction of the array of pressure sensing elements $32_1$ to $32_{63}$, and each of a plurality of predetermined reference distributions which is indicative of a corresponding one of a plurality of different relative positions of the array of pressure sensing elements 32 with respect to the radial artery 34. In the present embodiment, five different reference distributions as indicated in the respective boxes $38_1$ to $38_5$ of FIG. 2, are provided for the five correlation determination circuits 38, respectively. Each correlation determination circuit 38 is constituted by, for example, a sum-of-products calculation circuit as shown in FIG. 3. The calculation circuit includes an operational amplifier 42, and the same number of weighted resistors R as the number of the pressure sensing elements 32. In the present embodiment, sixty-three weighted resistors $R_1$ to $R_{63}$ are employed. The sixty-three weighted resistors $R_1$ to $R_{63}$ of each circuit 38 cooperate with each other to provide a corresponding one of the reference distributions. In this case, each correlation determination circuit 38 determines a correlation value $\gamma$ according to the following expression (1):

$$\gamma = \sum_{i=1}^{63} w_i \cdot t_i \quad (1)$$

wherein $w_i$, weighted resistance values of resistors $R_1$ to $R_{63}$, and $t_i$, voltage values of pulse wave signals SM applied to resistors $R_1$ to $R_{63}$.

The reference distribution provided for the first correlation determination circuit $38_1$ includes a portion indicated at a in the corresponding box of FIG. 2, which portion corresponds to the first to thirty-first pressure sensing elements $32_1$ to $32_{31}$. The thirty-one elements 32 corresponding to the portion of each correlation determination circuit 38 is utilized for determining an optimum pressing force to press the pulse wave sensor 18 and determining an optimum pressure sensing element 32 (described later). Similarly, the portion a of the reference distribution of the second correlation determination circuit $38_2$ corresponds to the ninth to thirty-ninth pressure sensing elements $32_9$ to $32_{39}$; the portion a for the third circuit $38_3$ corresponds to the seventeenth to forty-seventh elements $32_{17}$ to $32_{47}$; the portion a for the fourth circuit $38_4$ corresponds to the twenty-fifth to fifty-fifth elements $32_{25}$ to $32_{55}$; and the portion a for the fifth circuit $38_5$ corresponds to the thirty-third to sixty-third elements $32_{33}$ to $32_{63}$.

Each correlation determination circuit 38 generates an electric signal indicative of the determined correlation value $\gamma$, to a reference-distribution selection circuit 44. The selection circuit 44 is constituted by, for example, a hard wired logic circuit including comparators, AND circuits and OR circuits. The selection circuit 44 determines the greatest correlation value $\gamma_{max}$ out of the five correlation values $\gamma$ determined by the respective correlation determination circuits $38_1$ to $38_5$, and generates an electric signal to one of the five gates 40 of the selective transmission circuit 36 which one gate receives pulse wave signals SM from the thirty-one pressure sensing elements 32 corresponding to the portion a for the reference distribution or correlation determination circuit 38 which provides the greatest correlation value $\gamma_{max}$. Upon reception of the above indicated electric signal, the above indicated one gate 40 is opened so as to transmit the thirty-one pulse wave signals SM from the pressure sensing elements corresponding to the portion a, to a main device 50 of the present apparatus, via a multiplexer 46 and a pre-amplifier 48. In the event, for example, that the reference distribution for the second correlation determination circuit $38_2$ provides the greatest correlation value $\gamma_{max}$, the second gate $40_2$ is opened so that only the thirty-only pulse wave signals SM from the ninth to thirty-ninth pressure sensing elements $32_9$ to $32_{39}$ are supplied to the main device 50. Thus, in the present embodiment, the correlation determination circuits 38 serve as correlation determining means for determining a correlation between a distribution of magnitudes of the pulse wave signals as taken along the array of the pressure sensing elements, and each of predetermined reference distributions which is indicative of a corresponding one of different relative positions of the array of pressure sensing elements with respect to the radial artery; the reference-distribution selection circuit 44 serves as reference-distribution selecting means for selecting one of the reference distributions which provides the greatest correlation of all the correlations determined by the determining means; and the selective transmission circuit 36 serves as signal transmitting means for transmitting to the main device only the pulse wave signals generated from the pressure sensing elements in a portion of the array of pressure sensing elements which portion corresponds to the relative position indicated by the reference distribution selected by the selecting means.

The multiplexer 46 responds to a switch signal $SC_1$ (described later) to convert the received thirty-one pulse wave signals SM into a single signal, which is supplied to a demultiplexer 52 of the main device 50 via the pre-amplifier 48. The demultiplexer 52 restores the received signal to thirty-one pulse wave signals SM corresponding to the thirty-one pressure sensing elements 32 associated with the open gate 40. Each of the pulse wave signals SM is supplied to a central processing unit 58 via an amplifier 54 and an analog to digital (A/D) converter 56. The CPU 58 is connected to a read only memory 60, a random access memory 62, and a display 60 via data bus. In addition, the CPU 58 is connected to an output interface 66. The CPU 58 processes the received signals according to programs pre-stored in the ROM 60 by utilizing the temporary-storage function of the RAM 62, and generates switch signal $SC_1$ to the multiplexer 46 via the output interface 66 and, at the same time, a switch signal $SC_2$ to the demultiplexer 52 in synchronism with switch signal $SC_1$. In addition, the CPU 58 generates a drive signal SD to the pressure regulator valve 28 by utilizing the above indicated thirty-one pulse wave signals SM, and thereby regulates the fluid pressure in the pressure chamber 14 of the probe 10. While changing the pressure in the chamber 14, the CPU 58 determines an optimum pressing force to press the pulse wave sensor 18 against the body surface 20 and selects an optimum pressure sensing element 32 from the above indicated thirty-one pressure sensing elements 32, based on the shape of a curve representative of a distribution of the magnitudes of the thirty-one signals SM as taken along the direction of the array of elements 32. The technique of determining the optimum pressing force and the optimum pressure sensing element is described in detail in the previously indicated Publication No. 64-12505 of unexamined Japanese Utility Application. Therefore, no further description is provided. The CPU 58 utilizes pulse wave signal SM supplied from the optimum pressure sensing element 32 pressed at the optimum pressing force, as an optimum signal whose waveform accurately represents the pulse wave produced from the radial artery 34. The CPU 58 commands the display 64 to indicate, as the pulse wave of the subject, the waveform represented by the optimum signal.

As is apparent from the foregoing description, each of the correlation determination circuits 38 determines a correlation between a distribution of magnitudes of all pulse wave signals as taken along the array of the pressure sensing elements 32, and a corresponding one of the different reference distributions which is indicative of a corresponding one of the different relative positions of the array of pressure sensing elements with respect to the radial artery 34. Based on the correlations determined by the correlation determination circuits 38, the reference-distribution selection circuit 44 selects one of the reference distributions which one distribution provides the greatest correlation. One of the gates 40 of the selective transmission circuit 36 is opened, which one gate 40 is associated with the group of (i.e., thirty-one) pressure sensing elements 32 corresponding to the portion a of the reference distribution selected by the selection circuit 44. Consequently, only a small group of pulse wave signals from the selected pressure sensing elements 32 are supplied to the main device 50. Since the other pulse wave signals supplied from the other pressure sensing elements 32 are not necessary for determining the optimum pressing force or optimum pressure sensing element, or detecting the pulse wave, those pulse wave signals are discarded.

Even if a large number of pressure sensing elements 32 are used for increasing the length of the array of the pressure sensing elements 32 and simultaneously reducing the space between the pairs of adjacent pressure sensing elements 32, the signal transmission system (e.g., multiplexer 46) for transmitting to the main device 50 the pulse wave signals generated from the pressure sensing elements 32 is free from increased amount of burden, since the transmission system is required to transmit only a group of pulse wave signals, i.e., thirty one out of the sixty-three signals generated from the sixty-three elements 32, which group of signals are necessary and sufficient for determining the optimum pressing force to press the pulse wave sensor 18 and the optimum pressure sensing element 32. In addition, owing to this arrangement, the CPU 58 of the main device 50 is prevented from dealing with an increased number of pulse wave signals.

While, in the present embodiment, the sixty-three pressure sensing elements 32, the five correlation determination circuits 38, and the five gates 40 for the selective transmission circuit 36 are employed, it is possible to employ other appropriate numbers of elements 32, circuits 38 and/or gates 40.

Figure 4:
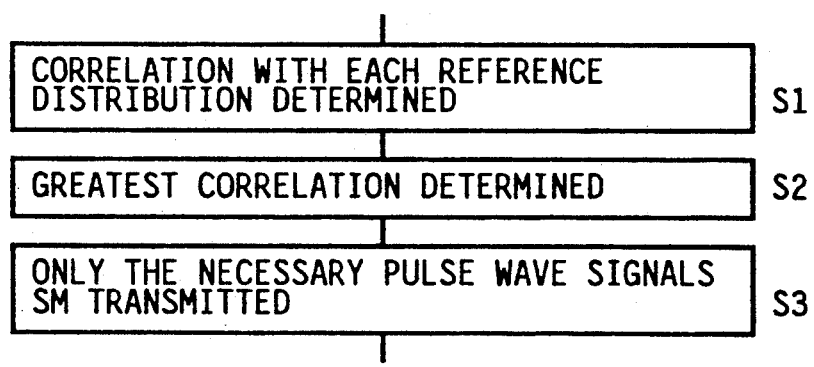
FIG. 4 is a flow chart utilized by another embodiment of the present invention.

In addition, while in the present embodiment the correlation determining means, reference-distribution selecting means, and signal transmitting means each are constituted by hardware, it is possible to constitute each means by software, for example, a microcomputer provided independently of the main device 50. The microcomputer is operated according to, for example, the flow chart of FIG. 4. The operation begins with Step S1 to determine a correlation between a distribution of magnitudes of pulse wave signals SM as taken along the array of the pressure sensing elements 32, and each of different reference distributions pre-stored in the microcomputer. Step S1 is followed by Step S2 to select one of the reference distributions which provides the greatest correlation of all the correlations determined in Step S1. Subsequently, Step S2 is followed by Step S3 to transmit to the main device 50 only pulse wave signals SM generated from the pressure sensing elements in an necessary portion of the array of pressure sensing elements which portion corresponds to the relative position indicated by the reference distribution selected in Step S2. In this case, Step S1 corresponds to the correlation determining means, Step S2 corresponds to the reference-distribution selecting means, and Step S3 corresponds to the signal transmitting means.

While the illustrated embodiments employ the multiplexer 46 and demultiplexer 52, it is possible to directly couple the outputs (i.e., pulse wave signals SM) of the selective transmission circuit 36 or the microcomputer, to the respective amplifiers 54 of the main device 50, without using the multiplexer or demultiplexer 46, 52.

In addition, although in the illustrated embodiments pulse wave is detected from the radial artery 34, it is possible to detect pulse wave from other arteries such as dorsal pedal artery or carotid artery, or alternatively it is possible to detect pulse wave from a vein.

While the present invention has been described in its presently preferred embodiments, for illustrative purposes only, it is to be understood that the invention is not limited to the details of the illustrated embodiments but the invention may be embodied with various changes, modifications and improvements that may occur to those skilled in the art without departing from the spirit and scope of the invention defined in the appended claims.

What is claimed is:

1. A pulse wave detecting apparatus, comprising:
a pulse wave sensor having a press surface on which a plurality of pressure sensing elements are provided in an array, said pulse wave sensor being adapted to be pressed at said press surface against a body surface of a subject such that the array of pressure sensing elements crosses over a blood vessel underlying said body surface, each of said pressure sensing elements generating an electric signal representative of a pulse wave transmitted thereto from said blood vessel via said body surface;
a main device receiving said electric signal from said each of said pressure sensing elements;
determining means for determining a correlation between a distribution of magnitudes of the electric signals as taken along said array of the pressure sensing elements, and each of a plurality of predetermined reference distributions which is indicative of a corresponding one of a plurality of different relative positions of said array of pressure sensing elements with respect to said blood vessel;
selecting means for selecting one of said reference distributions which provides the greatest correlation of all the correlations determined by said determining means; and
transmitting means for transmitting to said main device the electric signals generated from the pressure sensing elements in a portion of said array of pressure sensing elements which portion corresponds to the relative position indicated by the reference distribution selected by said selecting means.

2. The apparatus according to claim 1, wherein each of said pressure sensing elements comprises a pressure sensing diode.

3. The apparatus according to claim 1, wherein said array of pressure sensing elements extends over a length greater than a lumen of said blood vessel, and each of said pressure sensing elements is smaller than said lumen of the blood vessel.

4. The apparatus according to claim 1, wherein said determining means comprises a plurality of sum-of-products calculation circuits each of which includes an operational amplifier and a same number of weighted resistors as a number of said pressure sensing elements, the weighted resistors of said each calculation circuit having respective weighed resistance values which are representative of a corresponding one of said reference distributions, said reference distributions respectively corresponding to different small groups of pressure sensing elements in different portions of said array of pressure sensing elements.

5. The apparatus according to claim 4, wherein said determining means determines said correlation, $\gamma$, according to a following expression:

$$\gamma = \sum_{i=1}^{n} w_i \cdot t_i$$

wherein $w_i$; the weighted resistance values of the resistors of said each calculation circuit,
$t_i$; voltages of the electric signals applied to said resistors, and
n; number of said pressure sensing elements,
and generates a signal indicative of the determined correlation value, to said selecting means.

6. The apparatus according to claim 5, wherein said selecting means selects one of said reference distributions which provides the greatest correlation value, $\gamma_{max}$, of all the determined correlation values, and generates a signal indicative of the selected reference distribution, to said transmitting means.

7. The apparatus according to claim 6, wherein said transmitting means comprises a same number of gates as a number of said calculation circuits, and is responsive to said signal from said selecting means to open one of said gates which corresponds to said selected reference distribution and transmit to said main device only the electric signals generated from the group of pressure sensing elements corresponding to the selected reference distribution.

8. The apparatus according to claim 7, wherein said main device comprises a microcomputer and a display, said microcomputer including a central processing unit which processes the electric signals from said group of pressure sensing elements and thereby determines an optimum pressing force to press said pulse wave sensor against said body surface at which force said blood vessel is deformed to be partially flat, and an optimum pressure sensing element out of said pressure sensing elements which produces an electric signal accurately representing said pulse wave, said microcomputer commanding said display to indicate a waveform of the electric signal supplied from said optimum pressure sensing element.

9. The apparatus according to claim 1, further comprising coupling means for coupling said transmitting means to said main device to transmit the electric signals therebetween.

* * * * *